US007577743B2

(12) United States Patent
Fusari (10) Patent No.: US 7,577,743 B2
(45) Date of Patent: Aug. 18, 2009

(54) METHODS AND APPARATUS FOR PERFORMING CONTEXT MANAGEMENT IN A NETWORKED ENVIRONMENT

(75) Inventor: David Fusari, Groton, MA (US)

(73) Assignee: Sentillion, Inc., Andover, MA (US)

( * ) Notice: Subject to any disclaimer, the term of this patent is extended or adjusted under 35 U.S.C. 154(b) by 925 days.

(21) Appl. No.: 10/632,673

(22) Filed: Aug. 1, 2003

(65) Prior Publication Data

US 2005/0027784 A1 Feb. 3, 2005

(51) Int. Cl.
*G06F 15/173* (2006.01)
(52) U.S. Cl. .................................... 709/227
(58) Field of Classification Search ............. 709/213, 709/223
See application file for complete search history.

(56) References Cited

U.S. PATENT DOCUMENTS

| | | | |
|---|---|---|---|
| 5,930,786 A | 7/1999 | Carino, Jr. et al. | |
| 6,401,138 B1 | 6/2002 | Judge et al. | |
| 6,944,662 B2* | 9/2005 | Devine et al. | 709/225 |
| 6,986,060 B1* | 1/2006 | Wong | 726/26 |
| 6,993,556 B1* | 1/2006 | Seliger et al. | 709/203 |
| 7,016,942 B1* | 3/2006 | Odom | 709/212 |
| 7,143,195 B2* | 11/2006 | Vange et al. | 709/249 |
| 7,203,755 B2* | 4/2007 | Zhu et al. | 709/227 |
| 7,249,367 B2* | 7/2007 | Bove et al. | 725/60 |

FOREIGN PATENT DOCUMENTS

| | | |
|---|---|---|
| EP | 1 161 048 A2 | 12/2001 |
| WO | WO 00/59286 | 10/2000 |
| WO | WO 01/11464 A1 | 2/2001 |
| WO | WO 01/11464 A2 | 2/2001 |
| WO | WO 02/052420 A1 | 7/2002 |
| WO | WO 02/054699 A1 | 7/2002 |

OTHER PUBLICATIONS

"CCOW Tutorial" Presentation Jul. 25, 2003.
Search Report dated Sep. 22, 2005.
Anonymous: "CCOW Tutorial" Presentation, Jul. 25, 2003.
Clinical Context Working Group: "The Clinical Context Object Workgroup: Its Standards and Methods", CCOW, Feb. 16, 1998.
International Search Report, dated Dec. 14 2005.

* cited by examiner

*Primary Examiner*—David Y Eng
(74) *Attorney, Agent, or Firm*—Wolf, Greenfield & Sacks, P.C.

(57) ABSTRACT

Methods and apparatus related to context management in a networked environment are provided. According to one aspect, a technique is provided for facilitating communication between a client and a context management (CM) server, comprising establishing a network connection between the client and the CM server to enable communication, and maintaining the connection for the period of time during which the context is maintained.

49 Claims, 5 Drawing Sheets

METHODS AND APPARATUS FOR PERFORMING CONTEXT MANAGEMENT IN A NETWORKED ENVIRONMENT

FIELD OF THE INVENTION

The present invention relates to techniques for managing context among software applications in a networked environment.

BACKGROUND OF THE INVENTION

There exist commercial endeavors in which a plurality of computer applications share a set of entities or subjects which are common to the applications. For example, in the field of medicine, a user may provide input describing a given patient to multiple applications. The input may be clinical information, such as x-ray images or blood work results, financial information, such as insurance coverage or billing history, or other types of information. The user's task historically entailed repeating the entry of data identifying the patient into the multiple applications. Although patient data is an illustrative example, this practice extends to data describing other subjects as well, such as a user (i.e., to enable "single sign-on," wherein a user logs in to a single network-based resource and is automatically given access to other authorized network-based resources), patient encounter, clinical provider, observation, insurer, or other subject. The use of shared information among multiple applications is not limited to the medical field.

Data which describes a given subject, and which is used commonly by a plurality of applications, is referred to herein as a "context" defined by that subject. The desirability of managing context in the healthcare industry, so that a user need not repeatedly enter information for a subject into multiple applications, has been recognized. To this end, a standard for context management, known as the Health Level 7 (HL7) context management specification, was published in 1999 by the Clinical Context Object Workgroup (CCOW). The CCOW standard defines a context management architecture (CMA) and processes for managing information describing a subject across a range of clinical and other healthcare-related applications.

Among other features, the CCOW standard defines interfaces for inter-process communication, including communication between applications and a software-based module which coordinates the modification of data across applications (the "context manager"). One embodiment of a context manager is described in commonly-assigned U.S. patent application Ser. No. 09/545,396, which is incorporated herein by reference.

The interfaces ("technology mappings") defined by CCOW provide for communication between the context manager and various "styles" of applications, including those which follow the Microsoft Common Object Model (COM) and Hypertext Transport Protocol (HTTP) conventions, among others. For example, for a COM-based application, the CCOW standard specifies COM interfaces which allow the COM-based application to exchange data and parameters with the context manager when using a CCOW compliant context management system. The interfaces may be programmed to process COM-based data and parameters provided by the context manager and context participant applications to support the context management functions.

Figure 1:
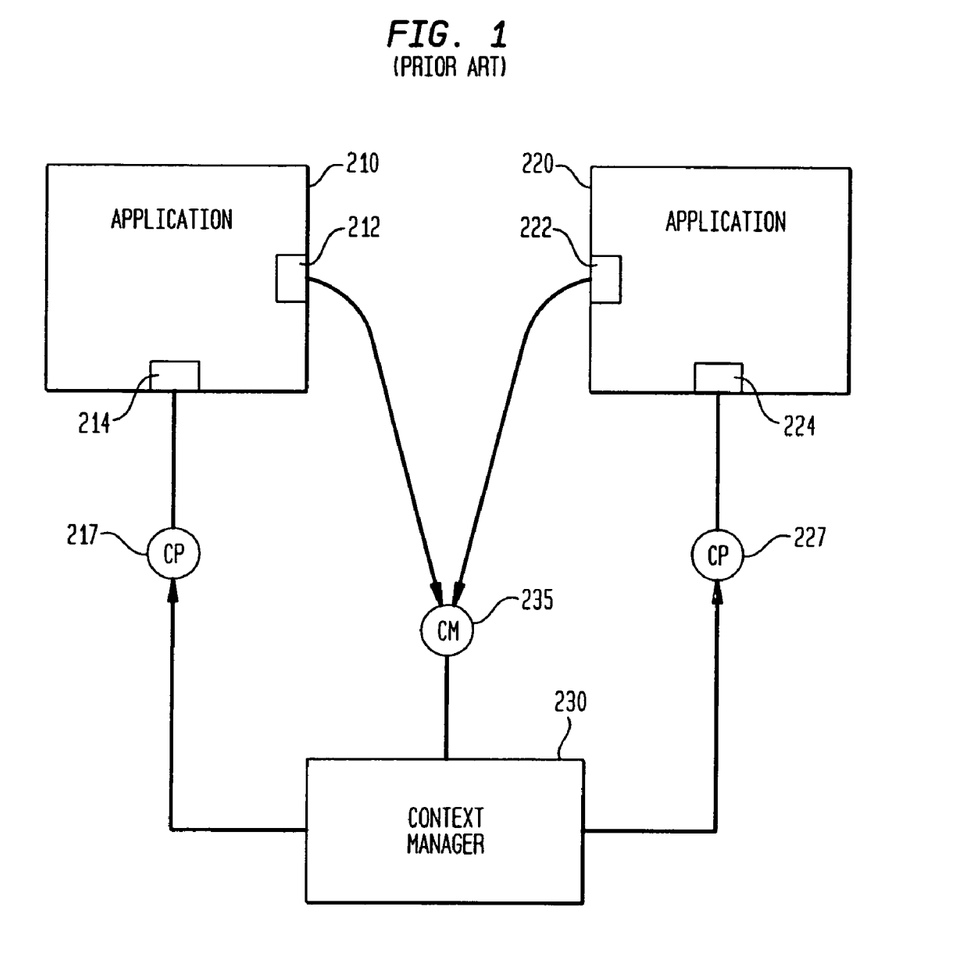
FIG. 1 depicts an exemplary implementation of a context manager and a plurality of context participant applications according to the prior art.

FIG. 1 depicts an exemplary context management system, in which a context manager 230 manages context for two context participant applications 210 and 220. Applications 210 and 220 may execute on the same or separate computers, and the computer(s) may be the same or separate from a computer on which context manager 230 executes. Communication between the processes may be enabled via any of numerous combinations of protocols and physical communications devices or components. For example, when the applications 210, 220 and/or the context manager 230 execute on the different computers interconnect by a network (e.g., a local area network), the TCP/IP protocol may be employed.

According to the CCOW standard, communication between the applications in a context and the context manager is facilitated through the use of context participant (CP) interfaces for the applications and a set of context manager (CM) interfaces for the context manager. Each of the CP and CM interfaces may comprise any of numerous suitable components for enabling inter-process communication. In one embodiment, each of the CP and CM interfaces is integrated in an associated application and provides a "plug" which enables communication with the application (e.g., CP interfaces 217, 227 may be implemented within applications 210, 220 respectively, and CM interface 235 may be implemented in an application program executing on the computer on which the context manager 230 executes). In the illustrative system of FIG. 1, the applications 210, 220 have CP interfaces 217, 227, respectively, associated with them.

Context participant (CP) interfaces 217 and 227, respectively, receive communications from context manager 230 on behalf of applications 210, 220. Applications 210, 220 may receive communications from the context manager 230 in a format and style commensurate with the CCOW standard (e.g., as COM messages or HTTP encoded messages over TCP/IP). In the embodiment shown, the communications pass through code portions 214 and 224 associated with the applications. CP interfaces 217, 227 may alternatively be incorporated directly into applications 210, 220 as described above, and directly pass communications thereto. As a further alternative, a CP wrapper or bridge can be provided that performs the function of the CP interface 217, 227, and allows an application to communicate according to the CCOW standard, without requiring any modification of the application itself. Context manager (CM) interface 235 receives communications from applications 210 and 220 and forwards those communications to the context manager 230.

As mentioned above, each of applications 210 and 220 includes a series of programmed routines integrated with the respective application code to perform context management support functions as defined by the CCOW standard. For example, applications 210 and 220 include code portions enabling communication with the context manager. Specifically, within application 210, code portion 212 defines messages sent to the CM interface 235, and code portion 214 implements the CP interface 217. Similarly, application 220 includes code portions 222 and 224 that, respectively, perform the same functions as code portions 212 and 214.

When a user of one of the applications (e.g., application 210) desires to switch the context by changing the data for a subject (e.g., switching from one patient to another), the application sends a request to the context manager 230 (via CM interface 235). The requesting application is referred to as an "instigator" of the requested change in the context.

When the context manager receives a request to change a subject of the context, context manager 230 surveys the other applications in the context (e.g., application 220), to determine whether the switch is acceptable to them. The context manager 230 performs the survey by sending a request to the other applications (e.g., application 220) via their associated CP interfaces. The other applications in the context may determine whether the subject change is acceptable or conditionally acceptable. While rules defining the acceptability of a subject change may be customized for specific applications and contexts, an example of a situation where a requested change may be conditionally acceptable is if data relating to the existing subject has not yet been written to permanent memory on the computer on which the application executes. In this example, the other application may respond to the survey by alerting the instigator that the data could be lost if a change proceeded. The surveyed applications respond to the survey by transmitting messages back to the context manager 230 describing their reactions to the requested change.

According to the CCOW standard, the context manager 230 communicates the results of the survey to the instigator application, and a user thereof examines the results and determines how to proceed. There are a range of options that the user can select, including canceling the requested change, executing the requested change, or removing the instigator application from the context. Any of these options can be selected by the user irrespective of the results of the survey. For example, if one or more of the surveyed applications indicates that the requested change is unacceptable to it, the instigator application may nevertheless force the context change, or alternatively, may simply remove itself from the context so that the instigator application can implement whatever changes it desires without impacting the other applications in the context. After the user decides how to proceed with the requested change, a call is made by the instigator application to the context manager 230 informing the context manager of the change decision. The context manager then makes one or more calls to publish the change decision by notifying the other applications in the context of the decision.

While CCOW supports context sharing among a number of different types of applications such as COM-based applications, HTTP or web-based applications, applications executed on a remote server and emulated on a client (e.g., using the Citrix MetaFrame and ICA client architecture), and others, CCOW does not define any implementation for enabling applications of different types to communicate in a manner that facilitates context sharing. In addition, in the example discussed above in connection with FIG. 1, it is assumed that communications can flow freely between the context manager and the computers on which the applications in the context are executing. However, in many networked environments that have security measures in place, that is not the case.

Various embodiments of the present invention are directed to techniques for performing context management in a networked environment.

SUMMARY OF THE INVENTION

One embodiment of the invention provides a method, in a system comprising a client, a context management (CM) server and a network that couples the client to the server, the client executing at least one client application that shares a context with another application for a period of time, the CM server executing a context management service to manage the context, of facilitating communication between the client and the CM server. The method comprises acts of: (a) establishing a connection, through the network, between the client and the CM server to enable communication between the CM server and the client; and (b) maintaining the connection between the client and the CM server for the period of time during which the at least two applications share the context. The act (a) may further comprise establishing a backchannel connection between the client and the CM server through TCP/IP.

Another embodiment of the invention provides a method, in a system comprising at least one client, at least one web server, and a context management (CM) server coupled to the at least one client and the at least one web server, the at least one client and the at least one web server executing a plurality of applications that share a context, the plurality of applications comprising at least one web application that is executed on the web server, the at least one client having at least one browser that enables the at least one client to access the at least one web application, the CM server executing a context management service to manage the context, of facilitating a requested change in at least one aspect of the context, the requested change being initiated by an instigator from among the plurality of applications. The method comprises acts of, in response to a change decision being reached as to whether each of the plurality of applications is amenable to the requested change: (a) publishing the change decision directly from the CM server to the plurality of applications; and (b) contacting the at least one browser directly from the CM server, so that the instigator need not contact the at least one browser, to inform the browser that its corresponding at least one web application has been updated.

Yet another embodiment provides a method, in a system comprising a first client, a context management (CM) server, a remote application server and at least one network that couples together the first client, the CM server and the remote application server, the remote application server executing at least one remote application, the first client executing at least one client application that may share a context with the at least one remote application, the first client further executing an emulation application that emulates that at least one remote application on the first client, the CM server executing a context management service to manage the context, of verifying that the at least one remote application is emulated on the first client and may belong to the same context. The method comprises acts of: (a) receiving from the first client first information that uniquely identifies an aspect of the first client; (b) receiving from the remote application server second information that uniquely identifies the aspect of a remote client on which the remote application is emulated; and (c) determining that the at least one remote application is emulated on the first client and may belong to the same context when the first information matches the second information.

Yet another embodiment provides a method, in a system comprising at least one client, a context management (CM) server, a plurality of remote application servers and at least one network that couples together the at least one client, the CM server and the plurality of remote application servers, the plurality of remote application servers comprising first and second remote application servers respectively executing first and second remote applications that are emulated on the at least one client and may share a context, the at least one client executing at least one emulation application that emulates the first and second remote applications on the at least one client, the CM server executing a context management service to manage the context, of verifying that the first and second remote applications are emulated on a same client and may belong to a same context. The method comprises acts of: (a) receiving from the first remote application server first information that uniquely identifies an aspect of the client on which the first remote application is emulated; (b) receiving from the second remote application server second information that uniquely identifies an aspect of the client on which the second remote application is emulated; and (c) determining that the first and second remote applications are emulated on the same client and may belong to the same context by examining the first information and the second information.

Yet another embodiment provides at least one computer-readable medium encoded with instructions for performing a method in a system comprising a client, a context management (CM) server and a network that couples the client to the server, the client executing at least one client application that shares a context with another application for a period of time, the CM server executing a context management service to manage the context, the method for facilitating communication between the client and the CM server. The method comprises acts of: (a) establishing a connection, through the network, between the client and the CM server to enable communication between the CM server and the client; and (b) maintaining the connection between the client and the CM server for the period of time during which the at least two applications share the context.

Yet another embodiment provides at least one computer-readable medium encoded with instructions for performing a method in a system comprising at least one client, at least one web server, and a context management (CM) server coupled to the at least one client and the at least one web server, the at least one client and the at least one web server executing a plurality of applications that share a context, the plurality of applications comprising at least one web application that is executed on the web server, the at least one client having at least one browser that enables the at least one client to access the at least one web application, the CM server executing a context management service to manage the context, the method for facilitating a requested change in at least one aspect of the context, the requested change being initiated by an instigator from among the plurality of applications. The method comprises acts of, in response to a change decision being reached as to whether each of the plurality of applications is amenable to the requested change: (a) publishing the change decision directly from the CM server to the plurality of applications; and (b) contacting the at least one browser directly from the CM server, so that the instigator need not contact the at least one browser, to inform the browser that its corresponding at least one web application has been updated.

Yet another embodiment provides at least one computer-readable medium encoded with instructions for performing a method in a system comprising a first client, a context management (CM) server, a remote application server and at least one network that couples together the first client, the CM server and the remote application server, the remote application server executing at least one remote application, the first client executing at least one client application that may share a context with the at least one remote application, the first client further executing an emulation application that emulates that at least one remote application on the first client, the CM server executing a context management service to manage the context, the method for verifying that the at least one remote application is emulated on the first client and may belong to the same context. The method comprises acts of: (a) receiving from the first client first information that uniquely identifies an aspect of the first client; (b) receiving from the remote application server second information that uniquely identifies the aspect of a remote client on which the remote application is emulated; and (c) determining that the at least one remote application is emulated on the first client and may belong to the same context when the first information matches the second information.

Yet another embodiment provides at least one computer-readable medium encoded with instructions for performing a method in a system comprising at least one client, a context management (CM) server, a plurality of remote application servers and at least one network that couples together the at least one client, the CM server and the plurality of remote application servers, the plurality of remote application servers comprising first and second remote application servers respectively executing first and second remote applications that are emulated on the at least one client and may share a context, the at least one client executing at least one emulation application that emulates the first and second remote applications on the at least one client, the CM server executing a context management service to manage the context, the method for verifying that the first and second remote applications are emulated on a same client and may belong to a same context. The method comprises acts of: (a) receiving from the first remote application server first information that uniquely identifies an aspect of the client on which the first remote application is emulated; (b) receiving from the second remote application server second information that uniquely identifies an aspect of the client on which the second remote application is emulated; and (c) determining that the first and second remote applications are emulated on the same client and may belong to the same context by examining the first information and the second information.

Yet another embodiment provides a context management server for use in a system comprising a client, the context management server and a network that couples the client to the context management server, the client executing at least one client application that shares a context with another application for a period of time. The context management server comprises: at least one processor to execute a context management service to manage the context; and at least one controller that maintains a connection through the network with the client for the period of time during which the at least two applications share the context.

Yet another embodiment provides a context management (CM) server for use in a system comprising at least one client, at least one web server, and a context management server coupled to the at least one client and the at least one web server, the at least one client and the at least one web server executing a plurality of applications that share a context, the plurality of applications comprising at least one web application that is executed on the web server, the at least one client having at least one browser that enables the at least one client to access the at least one web application. The CM server comprises: at least one processor to execute a context management service to manage the context; and at least one controller that: facilitates a requested change in at least one aspect of the context, the requested change being initiated by an instigator from among the plurality of applications; and in response to a change decision being reached as to whether each of the plurality of applications is amenable to the requested change: (a) publishes the change decision directly to the plurality of applications; and (b) contacts the at least one browser directly, so that the instigator need not contact the at least one browser, to inform the browser that its corresponding at least one web application has been updated.

Yet another embodiment provides a context management server for use in a system comprising a first client, the context management server, a remote application server and at least one network that couples together the first client, the context management server and the remote application server, the remote application server executing at least one remote application, the first client executing at least one client application that may share a context with the at least one remote application, the first client further executing an emulation application that emulates that at least one remote application on the first client. The context management server comprises: at least one processor to execute a context management service to manage the context; and at least one controller that: receives from the first client first information that uniquely identifies an aspect of the first client; receives from the remote application server second information that uniquely identifies the aspect of a remote client on which the remote application is emulated; and determines that the at least one remote application is emulated on the first client and may belong to the same context when the first information matches the second information.

Yet another embodiment provides a context management server for use in a system comprising at least one client, the context management server, a plurality of remote application servers and at least one network that couples together the at least one client, the context management server and the plurality of remote application servers, the plurality of remote application servers comprising first and second remote application servers respectively executing first and second remote applications that are emulated on the at least one client and may share a context, the at least one client executing at least one emulation application that emulates the first and second remote applications on the at least one client. The context management server comprises: at least one processor to execute a context management service to manage the context; and at least one controller that: receives from the first remote application server first information that uniquely identifies an aspect of the client on which the first remote application is emulated; receives from the second remote application server second information that uniquely identifies an aspect of the client on which the second remote application is emulated; and determines that the first and second remote applications are emulated on the same client and may belong to the same context by examining the first information and the second information.

Yet another embodiment provides a client computer for use in a system comprising the client computer, a context management (CM) server and a network that couples the client to the CM server. The client computer comprises: at least one processor to execute at least one client application that shares a context with another application for a period of time; and at least one controller that maintains a network connection with the CM server for the period of time during which the at least two applications share the context.

Yet another embodiment provides a method, in a system comprising an application computer executing an application that shares a context with at least one other application, a context management (CM) server executing a context management service to manage the context, a network that couples the application computer to the CM server, and a network security facility creating a boundary between a protected environment and an external environment, wherein one of the application computer and the CM server is disposed in the protected environment and the other is disposed in the external environment, and wherein the network security facility prevents direct connections between the application computer and the CM server from being initiated by the one of the application computer and the CM server disposed in the external environment, of facilitating communication between the application computer and the CM server. The method comprises acts of: (a) providing a gateway computer in the protected environment; (b) enabling the one of the application computer and the CM server that is disposed in the external environment to initiate a connection with the gateway computer; and (c) passing at least one communication, through the gateway computer, from the one of the application computer and the CM server disposed in the external environment to the other to enable the one of the application computer and the CM server disposed in the external environment to initiate communication with the other.

DETAILED DESCRIPTION

Aspects of the present invention are directed to facilitating context management in a networked environment. As used herein, context management refers to the sharing of numerous types of subject data, and includes the sharing of only user information in a single sign-on environment.

One issue that arises in networked environments relates to the use of virtual private networks (VPNs), network firewalls, or other security facilities which employ network address translation (NAT) or similar identity masking features. NAT converts the Internet Protocol (IP) addresses of client machines situated "behind" the firewall or VPN to one or more "masked" IP addresses which it presents to network components outside of the firewall. Though a NAT facility keeps track of messages being transmitted from a client behind a firewall to an outside device, and may perform a reverse conversion to allow a response to be sent back to the appropriate client while a connection is maintained, it effectively keeps client IP addresses hidden from outside devices so that the outside devices can not transmit unsolicited messages directly to the protected clients.

When the context manager executes on a server disposed outside a firewall employing NAT or other masking feature, it may be unable to initiate communication with a context participant application executing on a client behind the firewall. According to one aspect of the invention, a technique is employed for facilitating communication between a client and the context manager, whereby connection through the network is maintained between the client and the context manager for the period during which the client shares a context managed by the context manager.

In another aspect of the present invention, the CCOW standard is modified. As discussed below, according to the CCOW standard, the instigator application is charged with touching the browser for any web-based application in the context to inform the browser that a change decision has been published. Networked environments may exist wherein the instigator application and one or more browsers that correspond to web applications in the context are employed on opposite sides of a firewall or other security facility that effectively prevents direct communication between them.

Thus, in accordance with one embodiment of the present invention, the context manager touches the affected browsers, thereby making it unnecessary for the instigator application to directly communicate with the browsers that correspond to web applications in the context.

Two other embodiments of the present invention specifically relate to emulated applications, wherein the application is executed on a remote application server and is emulated on a client (e.g., the Citrix MetaFrame and ICA architecture mentioned above). In one embodiment, techniques are employed to ensure that an application executing on a remote application server belongs to a same desktop as the other applications in the shared context, to protect the integrity of the context. In another aspect, techniques are employed to ensure that two remotely executing applications are emulated on a same client, and can therefore belong to a same context, to protect the integrity of the context.

Figure 2:
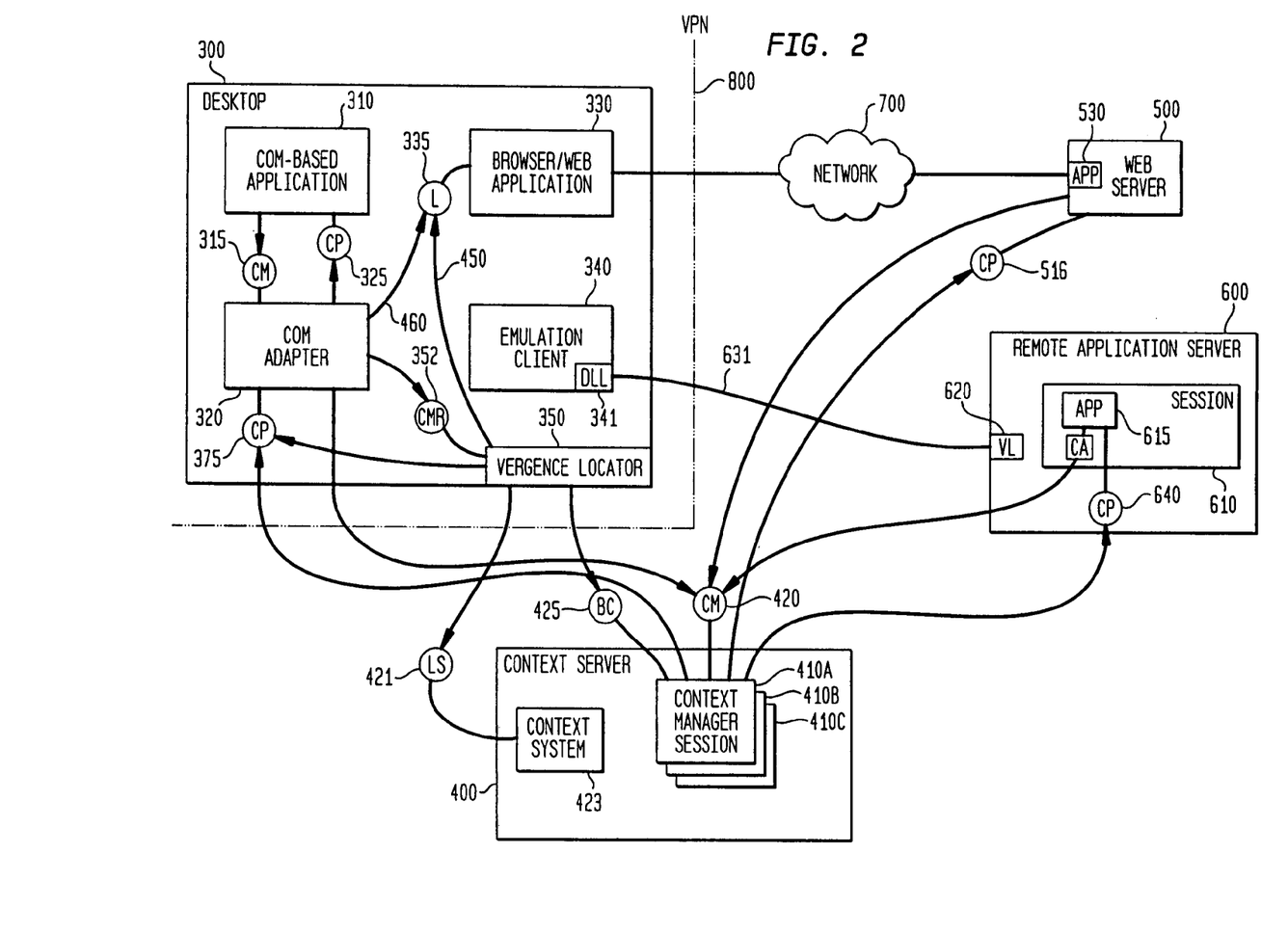
FIG. 2 depicts an exemplary context management system, implemented in a networked environment, in which aspects of the present invention may be implemented.

FIG. 2 depicts an exemplary context management implementation comprising a context manager and a number of context participant applications connected in a networked environment. It should be appreciated that various features and components of the system depicted in FIG. 2 are provided for illustrative purposes only, as the aspects of the present invention described below can be implemented on networked computer systems having numerous other configurations.

In the illustrative system of FIG. 2, a desktop 300 (which may be executed on a single computer) executes three basic types of applications i.e., a COM-based application 310, a browser 330 for a web-based application executing on a web server 500, and an emulation client 340 (e.g., a Citrix Independent Computing Architecture (ICA) client) emulating an application executing on a remote application server (i.e., a Citrix MetaFrame server) 600.

As discussed above, COM-based application 310 is an application which complies with Microsoft's Common Object Model. For example, application 310 may be a Windows-based application which is used to maintain, for example, patient x-ray data, although numerous other possibilities exist.

In the embodiment shown, desktop 300 also includes a COM adapter 320 to facilitate communication between applications that employ different communication protocols (e.g., application 310 which uses COM-based standards for communication and application 530 on web server 500 that uses web-based protocols). In the embodiment shown, COM adapter 320 translates COM-based communication from application 310 to HTTP-based communication, and translates HTTP-based communication to COM-based communication for receipt by application 310. COM adapter 320 may have a series of programmed routines designed to perform this translation. However, the COM adapter is not limited in this regard, as it may be implemented in software, hardware, firmware or combinations thereof. In addition, it should be appreciated that the present invention is not limited to use on a system employing a COM adaptor that performs any particular type of translation between communication formats, as the present invention can be used upon a system that enables communication between applications employing different communication protocols in any suitable manner.

For example, although the implementation depicted provides for inter-process communication using HTTP, other implementations may provide for communication using various other protocols. As such, other translation facilities can be employed rather than COM adapter 320. In some implementations, no translation facility at all is employed (e.g., if no COM-based applications are employed or if the applications are capable of communicating using a common protocol).

In the embodiment shown, COM adapter 320 accepts outgoing communication from application 310 at a CM interface 315. The COM adapter 320 translates those COM-based communications to HTTP-based communications, and transmits them to the CM interface 420 of a context manager session 410A executing on a context management server (referred to as a context server) 400. Similarly, COM adapter 320 receives at CP interface 375 incoming messages, in HTTP format, that are transmitted from the context server 400 to application 310, translates those communications to the COM-based protocol and forwards them to the CP interface 325 for the application 310.

As mentioned above, the desktop 300 also executes a browser 330. Brower 330 communicates with a web server 500 via a network 700. As defined herein, the term "browser" refers not only to web-based applications conventionally referred to as browsers, but also any other application (e.g., implemented using Java applets) that sends or receives data using HTTP (or other web-based protocol), and that, like a web-based browser, separates the user interface from the corresponding application program in a manner such that updates of the application program are not automatically sent to the user interface. Similarly, web server 500 may comprise any suitable hardware, software or combination thereof configured to send and receive web-based communication. Network 700 may comprise the Internet, a local area network (LAN), other communications infrastructure, or combinations thereof, and may use any suitable communications protocol.

Web server 500 executes a web-based context participant application 530. In a conventional manner, browser 330 may display information (e.g., web pages) transmitted by application 530, and accept input from a user (e.g., in the form of keystrokes, mouse movements and the like), and transmit those inputs to application 530 for processing. However, the present invention is not limited to use with web-based applications that are implemented in any particular manner, as browser 330 and web server 500 may distribute processing associated with application 530 in any suitable manner.

The illustrated desktop 300 also executes a emulation client 340, which is in communication with a remote application server 600 to initiate a session 610 within which one or more context participant applications may execute. The emulation client 340 may establish session 610 and contact the remote application server 600 to obtain a set of available applications. In response, the server 600 may transmit a list of applications available for use, using any of numerous techniques. For example, when using the Citrix MetaFrame and ICA client architecture, a set of available applications may be transmitted over the Citrix ICA protocol. In the illustrative implementation depicted, remote application 615 has been selected by the user as a context participant and is a COM-based application. In the embodiment shown, the remote application server 600 includes a COM adapter (CA) 617 that translates COM-based communications from the application 615 to HTTP-based communication (and vice versa) for communication with the CM interface 420 of the context manager session 410A, in much the same manner as the COM adapter 320 discussed above.

Input to the remote application 615 (e.g., in the form of keystrokes and mouse movements), is sent from emulation client 340 to server 600 via connection 631 (e.g., a virtual channel created using the Citrix ICA protocol), and commands embodying resulting screen changes in the user interface on client 340 are returned from the server 600 to the emulation client 340 via connection 631. The connection 631 can be implemented over any physical communication medium, including the same network 700 that connects the desktop 300 to the web server 500. In addition, the same network 700 may also be used for communication between the desktop 300 and the context vault 400, as well as between the context server 400 and each of the remote application server 600 and web server 500. However, the present invention is not limited in this respect, as the embodiments of the present invention can be implemented on any type of computer system configuration, including systems using any type of interconnections between the various system components.

Desktop 300 may comprise any of numerous computing facilities capable of executing the applications discussed above, as the embodiments of the present invention are not limited to use with any desktop computing platform. For example, desktop 300 may comprise a personal computer, server, handheld computing device, or other type of computing facility. Additionally, although COM-based applications typically execute in a Windows environment, desktop 300 is not limited to the execution of any particular operating system.

In the embodiment shown, context server 400 executes multiple context manager sessions 410A-C. However, the embodiments of the present invention are not limited to use with a context management server capable of executing multiple context manager sessions. Furthermore, the embodiments of the present invention described herein can alternatively be employed in a system that includes multiple context servers, each capable of executing one or more context manager sessions. In one embodiment, context server 400 is implemented as a server appliance, as described in commonly assigned U.S. patent application Ser. No. 09/583,301, which is incorporated herein by reference. However, the embodiments of the invention are not limited to use with a context management server implemented in this manner, as the context server 400 may comprise any suitable computing platform, such as a general-purpose server or other computing device. Indeed, although context server 400 is depicted in FIG. 2 as a device which is separate from desktop 300, the system is not limited in this regard, as the context manager session can be executed on the desktop 300.

In the system depicted in FIG. 2, context manager session 410A manages context for all the applications represented, including COM-based application 310, web-based application 530, and the remote application 615. To communicate with COM-based application 310, context manager session 410A transmits messages to COM adapter 320 via CP interface 375, and receives messages from COM adapter 320 via CM interface 420. To communicate with web application 530, context manager session 410A transmits messages to web server 500 via CP interface 510 and receives messages from web server 500 via CM interface 420. Finally, to communicate with the remote application 615, context manager session 410A transmits messages to COM adapter 617 executing on remote application server 600 via CP interface 640, and receives messages from COM adapter 617 via CM interface 420.

Conventionally, TCP/IP communication between a browser and web server is only initiated by the browser for security reasons. Specifically, if a web server knew the identities of the browsers with which it communicates, a security breach at the server could give an intruder the identity of a number of vulnerable targets. For this reason network restrictions are typically employed so that the server responds to communications from the browser, but does not initiate such communications.

When a web application participates in a context, it may be the application (e.g., application 530 in FIG. 2) executing on the web server that is the context participant, rather than the browser. As discussed above, in accordance with the CCOW standard, when a change to the context is executed, the context manager publishes the change decision to the applications in the context. In the case of a web application, when the change in context occurs, the change takes place in the application 530 on the web server 500. However, because the web server does not initiate communication with the browser, the browser 330 may not be automatically made aware of the change, such that the representation of the state of the application 530 on the desktop 300 may be inaccurate. Thus, in accordance with one embodiment of the present invention, a technique is employed to enable a browser to be made aware that a change has taken place in a corresponding web application, so that the browser can request the web server to provide it with updated information.

In accordance with the CCOW standard, a listener 335 is employed to assist in instructing the browser 330 to request updated information from its corresponding web server 500 when a change has been made to the web application 530 executing thereon. In the CCOW standard, the listener 335 provides an interface that the instigator application can contact to inform it that a change in the context has been made, so that the listener 335 can instruct the browser 330 to go back to the web server 500 for an update. The listener 335 can be implemented as a stand-alone module, as part of the browser 330, or as part of any other component of the desktop 300, as the present invention is not limited to any particular implementation.

The updating of the listener 335 can, similarly, be implemented in any of numerous ways. In accordance with one embodiment of the present invention, when the context manager (e.g., session 410A) returns the survey information to the instigator application relating to a requested change, the context manager also provides a list of URLs (corresponding to the listeners for any web-based applications in the context) to the instigator application, instructing the instigator application to contact (or "touch") those URLs to inform them that the context has been updated.

As shown in FIG. 2, when the instigator application is another application executing on the same desktop 300 as the browser 330 (e.g., the COM-based application 310), the instigator application can directly (e.g., through the COM adapter 320) contact the listener 335, as the URL for the listener 335 will be accessible from within the desktop.

Communication between the instigator application and the listener 335, like other communication between different computers in the context management architecture discussed above, is complicated when two or more of the computers are on opposite sides of a firewall, VPN or other security facility that employs NAT. In the illustrative implementation shown in FIG. 2, such a VPN 800 is shown around the desktop 300. Because of the VPN 800, components of the computer system that are not on the desktop 300 may have difficulty in initiating communication with any of the components on the desktop, such as the listener 335 or the COM-based application 310.

For example, if COM-based application 310 initiates a context change, it may send a communication to context manager session 410A. The communication will be altered by VPN 800 to obfuscate the true identity (typically expressed as the IP address) of the originating application within the VPN 800. As a result, an originating IP address of, for example, "172.20.10.5" may be changed to another address such as "10.10.10.5". With a masking utility such as NAT, once a connection has been established (e.g., between the COM adapter 320 and the context server 400), bidirectional communication through that connection (or open channel) is supported. For example, a masking utility such as NAT may keep track of the outgoing communication so that it can route a response back to the sender of an originating message (e.g., if context manager session 410A responds to application 310 at IP address "10.10.10.5", the masking feature may perform a reverse conversion, thereby directing the message back to IP address "172.20.10.5").

While components within the VPN 800 can initiate communication with components outside the VPN, the reverse is not true. For example, if context manager session 410A sends an unsolicited message (for example, a survey issued as a result of another application seeking to instigate a context change) intended for application 310 at either of IP addresses "10.10.10.5" or "172.20.10.5", the VPN 800 may refuse to let the message pass. A similar problem is encountered when an application outside of the VPN 800 is an instigator application that seeks to contact the listener 335 to instruct it to touch its browser to seek an updated page from its corresponding web server in response to a context change. In this respect, the URL that the context manager will provide to the instigator application along with the survey results is the URL that the listener 335 passes along to the context manager as its contact address. However, the URL will be an address accessible only within the VPN 800, such that any attempt to access the listener 335 from an instigator application outside of the VPN 800 will be unsuccessful.

In accordance with the CCOW standard, a desktop executing a COM-based or web-based application also includes a Context Management Registry (CMR) interface that the desktop can query to determine the identity (e.g., find the URL for) a context manager to manage a context. In the embodiment of the invention illustrated in FIG. 2, the CMR interface 352 is implemented by a vergence locator 350 provided on the desktop 300, with the CMR interface 352 being a plug into the vergence locator 350. The CMR interface 352 can be queried by the COM-based application 310 (via the COM adapter 320) or the browser 330 to request the identity of the appropriate context manager (e.g., one of the context manager sessions 410A-C). When a context is initially being established (such that no context manager has been assigned to it), the vergence locator 350 uses a URL provided in the CMR interface 352 to contact the context management server (e.g., context server 400) to initiate a context session. The communication from the vergence locator 350 to the context server is directed to a location service (LS)(having a plug 421) that forms part of a context system 423 that manages the multiple context manager sessions 410A-C. Thus, this communication goes through a private interface, rather than through the CM interface 420 for any context manager session. However, it should be appreciated that the present invention is not limited in this respect, and that communication between the vergence locator and the location service in the context system 423 can be accomplished in any suitable manner.

When the vergence locator 350 contacts the location service of the context system 423 to request a new context manager session, the context system 423 initiates a new context manager session 410A-C and returns to the vergence locator 350 a URL that uniquely identifies the CM interface 420 for the new context manager session.

In the embodiment shown, the browser 330 can obtain the URL, via the vergence locator, from the context manager and provide it to its corresponding web application 530, which may then access the context manager directly in the manner described below.

In the illustrative embodiment shown, each remote application server executing an application that may share a context (e.g., server 600) also includes a vergence locator 620 that performs functions similar to the vergence locator 350, including the implementation of a Context Management Registry interface (not shown) that enables the remote application server to locate the URL for the context manager and initiate a context management session in the manner discussed above.

One aspect of the invention provides a technique for facilitating communication between two components on opposite sides of a security facility in a system that implements context management. In one embodiment, the technique involves establishing a network connection between the desktop (or remote application server) and the context manager, and maintaining the connection for the period of time during which any of the applications on the desktop (or the remote application server) share a context that either (1) includes one or more participant applications executing on a computer on the opposite side of a security facility or (2) is managed by a context manager executing on a computer on the opposite side of a security facility. According to one embodiment, the connection is a TCP/IP back-channel connection between the context management server (e.g., context server 400) and the client (e.g., desktop 300 or remote application server (e.g., server 600), which may be initiated by a client or remote server communication to the context management server, as described below. However, this aspect of the present invention is not limited in this regard, as any connection which is maintained over the relevant period of time may be employed.

In one embodiment, when a context environment is initially set up, a TCP/IP back-channel is established between the context management server (e.g.) vault 400A and the vergence locator 350 on the client desktop 300. The TCP/IP back-channel is a durable connection that lasts beyond the specific communication session necessary to establish the context environment, but rather, is maintained during the entire time period during which an application on the desktop 300 shares a context either with another application on the opposite side of a security facility (e.g., VPN 800), or participates in a context managed by a context manager on the opposite side of a security facility. The back-channel provides an open communication path from the context server 400 to the desktop 300, so that a context manager session (e.g., 410A) can initiate communication with the desktop 300, or pass along communications to the desktop 300 from one of the other applications (e.g., the web-based application 530 or the remotely executing emulated application 615) in the context.

One exemplary implementation of the embodiment of the present invention that employs a backchannel between the vergence locator and the context manager is shown in FIG. 2. Each context manager session 410A-C can include a backchannel (BC) plug 425 that can be used for communication with the vergence locator to establish the backchannel. In FIG. 2, only one backchannel plug 425 and one CM interface 420 is shown, but it should be appreciated that one of each may be provided for each context session. Thus, in the embodiment shown, the backchannel communication does not pass through the context manager interface 420 for the context manager session. However, it should be appreciated that the embodiment of the present invention that employs a backchannel is not limited to any particular implementation, as numerous alternative implementations are possible.

According to one embodiment, the vergence locator 350 receives communication via the back-channel from context manager 410A and relays it to the appropriate entity on the desktop 300. For example, if context manager 410A issues a survey communication intended for COM-based application 310 to determine whether a context change instigated by web application 530 is acceptable, context manager 410A can transmit the communication via the back-channel to vergence locator 350. The ultimate destination for the communication can be identified in any of numerous ways, such as by a URL previously provided by the desktop 300 to the context server 400 for such communications (e.g., a URL for the CP interface 375). Because the CP interface 375 and the vergence locator 350 are both behind the VPN 800, the vergence locator 350 can forward the communication directly to the specified URL for the CP interface 375 using any suitable technique. The CP interface 375 will then forward the communication to the COM-based application 310 in the manner discussed above. It should be appreciated that the manner in which the vergence locator 350 identifies the appropriate entity in the desktop 300 to which communications received over the back-channel are relaying is not limited to any particular implementation, as numerous techniques are possible.

In the manner described above, a context manager executing on a server outside a firewall or other security facility may initiate communication with applications executing behind a firewall, using a technique which does not require knowledge of the IP address for any entity on the desktop.

In one embodiment of the present invention, techniques are employed to ensure that when a connection (e.g., the back-channel connection discussed above) is established between a desktop or remote application server and the context management server, the connection is secure, such as by verifying that the desktop or remote application server is authorized to establish the connection. In one embodiment, the verification is performed using digital signatures, although the present invention is not limited in this respect, as any suitable technique may be employed.

In one embodiment of the present invention, heartbeat or pinging techniques can be employed between the desktop 300 and the context server 400 to ensure that the back-channel path remains open, so that in the event that the back-channel is lost for any reason, it can be re-established by the desktop 300.

It should be appreciated that a remote application server (e.g., the server 600) may also be configured in computer systems wherein they are protected by a security facility, such as a firewall or VPN. Thus, in accordance with one embodiment of the present invention (not shown), a back channel can similarly be established between the vergence locator 620 of the remote application server 600 and the context server 400 in a manner similar to that discussed above. It should be appreciated that a back-channel can similarly be formed between the context server 400 and a web server executing an application in a shared context, but that such a back-channel will normally be unnecessary in view of the fact that web servers are typically exposed, rather than being protected behind a security facility, such that the context server 400 can typically initiate communications directly with a web server.

Figure 4:
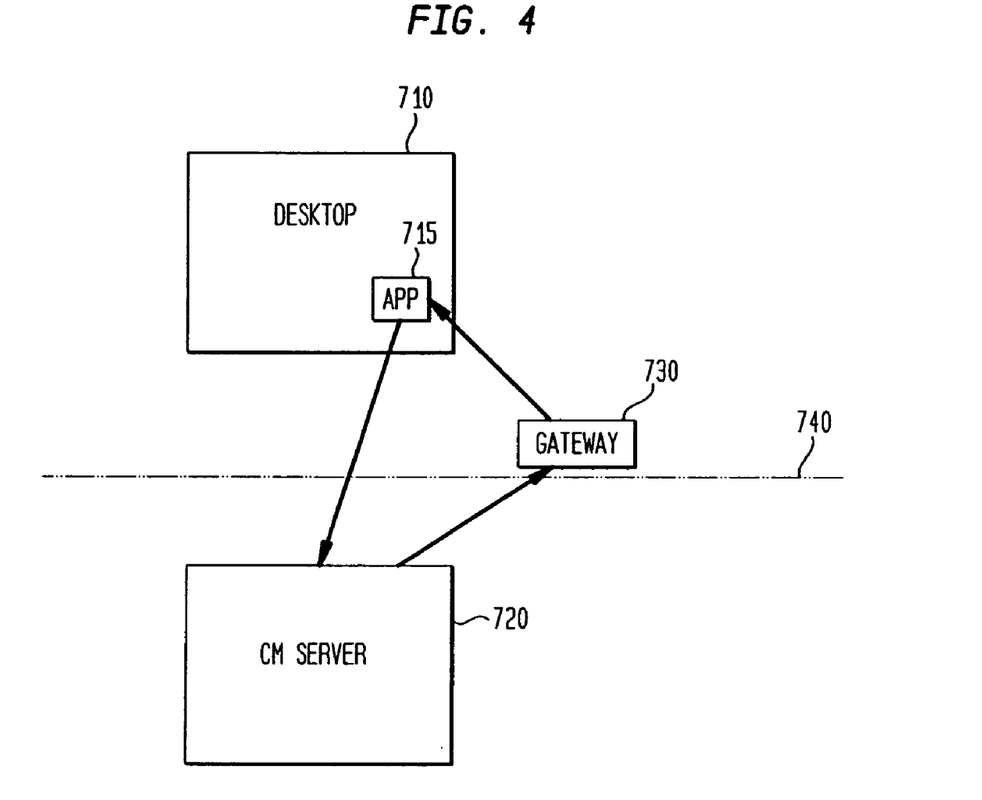
FIG. 4 depicts an exemplary system configuration in which a client application and a context management server are disposed in protected and external areas created by a network security facility, respectively, and on which aspects of the present invention may be implemented.
Figure 5:
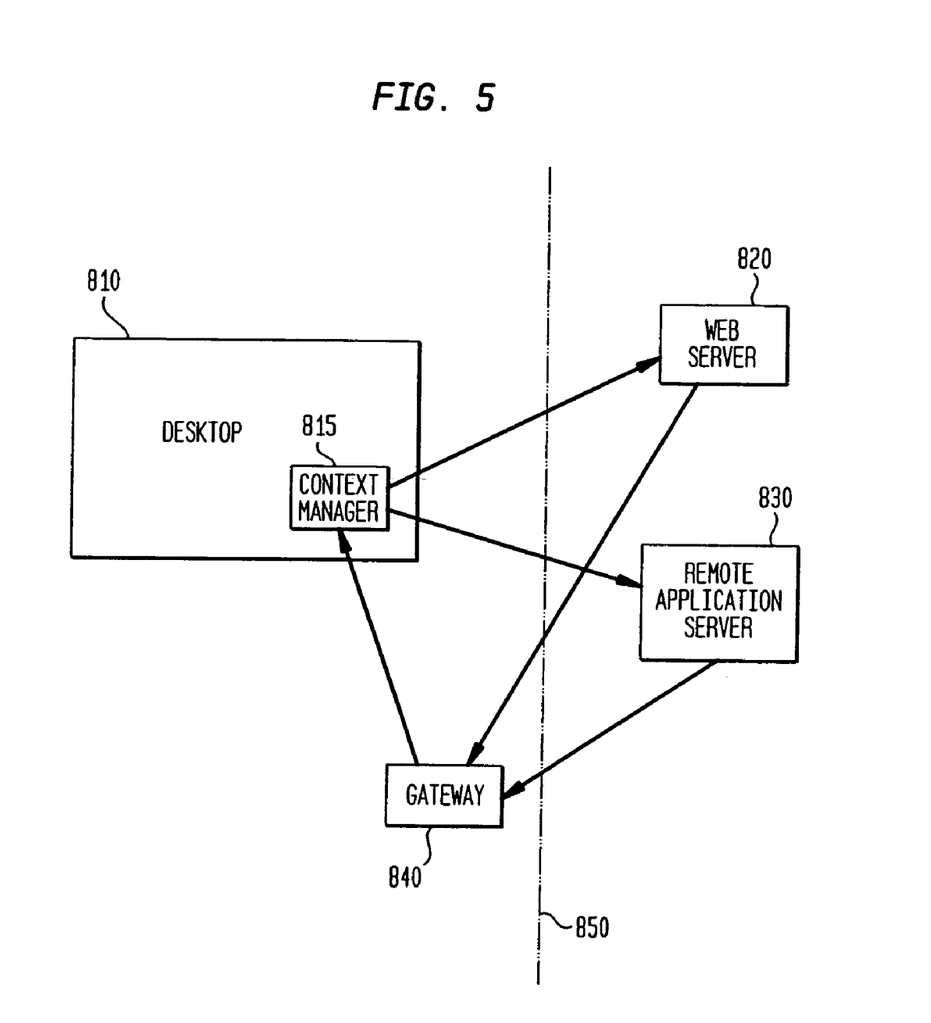
FIG. 5 depicts an exemplary system configuration in which server applications and a context management server are disposed in external and protected areas created by a network security facility, respectively, and on which aspects of the present invention may be implemented.

In another embodiment of the present invention, communication between the context manager and a context participant application is facilitated across a firewall without requiring a durable network connection to be maintained throughout the life of the context. It should be appreciated that there are at least two alternate configurations in which the context manager can be on the other side of a firewall from a context participant. An illustrative example of a first is depicted in FIG. 4, in which context participant application 715 executes on desktop 710 behind firewall 740, while context management server 720 is disposed outside the firewall 740. An illustrative example of a second configuration is depicted in FIG. 5, in which the context manager 815 executes on desktop 810 behind firewall 850, while separate context participant applications execute on web server 820 and remote application server 830, which are each disposed outside the firewall 850.

According to one embodiment, described with reference to the configuration depicted in FIG. 4, communication from a context management server 720 to a context participant application 715, disposed behind a firewall 740, is enabled with a context participant gateway 730. In the embodiment shown, context participant gateway 730 is implemented on a separate server, and a "small" hole in the firewall 740 is provided to enable limited communication thereto. That is, the communication that passes through the firewall 740 can be limited to communications that originate from the context management server 720, and/or are of the specific types employed in the context management protocol for communication from a context manager to a context participant. Communication from the context manager 720 to context participant application 715 is routed through the context participant gateway 730 to the participant application 715 in any suitable manner. For example, techniques can be employed that are similar to those discussed above wherein communication from the context manager is sent to the vergence locator 350 (FIG. 2) and forwarded to the context participant application, with the exception that the context participant gateway 730 may be disposed on a different computer from the context participant application, whereas the vergence locator is provided on the same desktop. In this manner, the context participant gateway 730 can allow only communications directed to a context participant application (or associated listener) to pass through the firewall.

In an alternate embodiment, described with reference to the configuration depicted in FIG. 5, communications from context participant applications running on servers 820, 830 to a context manager 815, which is disposed behind firewall 850, are enabled in an analogous manner with context manager gateway 840. As with the configuration depicted in FIG. 4, the context manager gateway 840 may be provided on a separate server, and a "small" hole in the firewall can be employed to allow communication to the context manager gateway 840, but only from computers 820, 830 which are recognized to be executing context participant applications, and only communications directed to the context manager 815. The context manager gateway 840 can forward such communications to the context manager 815 in a manner similar to that described above. As described above, one configuration wherein a context manager gateway may be useful is when the context manager is provided on a desktop with one or more context participant applications.

Referring again to FIG. 2, remote application 615 executes within a session 610 on server 600. In the implementation depicted, server 600 is a separate computer from desktop 300, and is disposed on the opposite side of VPN 800, so that the remote application server 600 cannot send unsolicited communication to applications executing on desktop 300. As discussed above, the CCOW standard specifies that when an application instigates a context change, the context manager supplies a list of listeners for web-based applications in the context, and the instigator application touches those listeners when the change decision is published. Thus, when the remote application 615 is the instigator of a change request, the VPN 800 prevents it from touching the listener 335 executing on the desktop 300 when a change decision is published.

In accordance with one embodiment of the present invention, a modification to the CCOW standard is implemented, wherein rather than having the instigator application touch the listeners for any web-based context participants when a change decision is published, the context manager touches the listeners. This aspect of the present invention can be used in conjunction with the embodiment of the present invention discussed above wherein an open communication channel is maintained between the context server 400 and any of the computers that have an application executing in the context and are behind a security facility, so that the context manager has the ability to touch the listener for each of the web-based applications in the context.

As discussed above, in the CCOW standard, when an instigator application requests a context change, the context manager conducts a survey of the other applications in the context, and returns the results to the instigator application, along with a list for the instigator application to use to touch the listeners for any web-based participants. In accordance with one embodiment of the present invention, a list of listeners to be notified need not be returned to the instigator application, as the instigator application need only inform the context manager of the decision, and the context manager publishes the decision and contacts the listeners directly.

The inclusion of remote application servers (such as server 600) within a context management system raises additional concerns regarding the integrity of a context. For example, when a plurality of context participants includes a remote application (e.g., application 615) and one or more desktop applications, it may be desirable to verify that the remote application and the desktop application(s) are associated with the same client (e.g., that the emulation client 340 and COM-based application 310 execute on the same desktop 300), to guard against a rogue application intruding in a context. Accordingly, one embodiment of the invention provides a technique to match a remote application to the client device on which it is emulated. In one embodiment, a unique client identifier is received from the client and from the remote server, and the identifiers are compared to determine whether the remote application is emulated on a "trusted" client, e.g., one that includes another application in the context.

In one embodiment, the vergence locator 620 issues a command to the emulation client 340 requesting a unique identifier for the client. The client 340 queries desktop 300 for an identifier which uniquely identifies the desktop, and transmits a response back to the remote application server 600. This may be accomplished using any of numerous suitable techniques. In one embodiment, the emulation client 340 calls a dynamic link library (DLL) to query desktop 300 for at least one Media Access Control (MAC) address, which is a unique hardware identifier assigned to each of the desktop's network adapters. The MAC address is then returned to the remote application server 600. The context server 400 similarly queries desktop 300 (e.g., over the back-channel) for the MAC address. Thus, when an application executing on the remote application server 600 seeks to be added to a context, it provides the MAC address it receives for the client to the context server 400, which compares that MAC address with one received directly from the client. A matching set of MAC addresses confirms that remote application 615 is emulated on an emulation client 340 on the same desktop on which other context participant applications execute, so the remote application is added to the context. Alternatively, if the MAC addresses do not match, the remote application is not added to the context, because it is not emulated on the same desktop as the other applications in the context.

The desktop may comprise multiple network adapters. In one embodiment, the DLL is configurable to concatenate, or otherwise combine or modify, multiple MAC addresses to form a single unique identifier that can be used in the above-described matching process. It will be appreciated that the embodiment of the present invention that employs a MAC address (or some unique identifier derived therefrom) is not limited to concatenating or combining multiple MAC addresses in any particular way, as any suitable technique can be employed, including the selection of a particular one of the MAC addresses for use as the unique identifier.

Communication between the remote application server 600 and the emulation client 340 to receive a unique identifier can be accomplished using any suitable technique. In one embodiment for use with the Citrix MetaFrame and ICA client architecture, the Citrix-provided capability to implement a virtual channel on top of connection 631 between the client and server is used to transmit information between the Citrix MetaFrame server 600 and the Citrix ICA client 340.

Verifying that a remote application and other context participants originate from the same client may be performed in any of numerous ways, as the invention is not limited to the above-described techniques. For example, the unique client identifier need not be a MAC address, and can be any information that can be used to identify the client.

In some computer system configurations, an emulation client 340 may emulate multiple remote applications which each execute on different remote application servers. In accordance with one embodiment of the present invention, a technique is employed to ensure that the multiple applications executing on different remote application servers belong to the same emulation client, and therefore are on the same desktop and can share a context. In a manner similar to that described above, this prevents a rogue application from improperly intruding into a context.

In accordance with one embodiment of the present invention, an identifier that uniquely identifies the emulation client 340 is requested by each remote application server, and is provided from the remote application server to the context manager. The context manager further requests the unique identifier(s) directly from the emulation client, and then compares the identifiers to ensure a match in much the same manner as discussed above. In accordance with one embodiment of the present invention, the unique identifier may be a hardware MAC address (or any other suitable identifier) as discussed above.

It should be appreciated that a desktop machine on which a client emulation program executes may be incapable of providing its MAC address. For example, in some system configurations, a facility such as the DLL described above may not be present, such as a configuration in which a user employs an unmodified laptop computer to dial into a remote application server. Thus, one embodiment of the present invention provides for an alternative identifier to be employed to uniquely identify the emulation client.

In accordance with one embodiment of the present invention for use with the Citrix MetaFrame and ICA client architecture, an embodiment of the present invention makes use of a Citrix application programming interface (API) that provides information relating the client. In accordance with the Citrix-provided API, the login of the user on the client, and the IP address and a client host name (that typically defaults to the name of the computer on which the client is executing) for the client machine can be provided.

In accordance with one embodiment of the present invention, these three pieces of information are employed to verify a match of the client, such that each of the three pieces of information must be identical for a match to be recognized. Thus, when a user at a single emulation client logs into two remote application servers, in accordance with one embodiment of the present invention, the user employs the same login identifier on both. The two remote application servers use the Citrix-provided API to retrieve the above-described identifier information from the client and provide the identifier information to the context manager. The context manager verifies that the identifier information matches to determine that the two remote applications are emulated on the same emulation client, and can therefore belong to the same context.

It should be appreciated that the embodiment of the present invention that collects unique identifier information from the client machine is not limited to employing the Citrix-provided API to collect information, as other implementations are possible. In addition, it should be appreciated that the aspects of the present invention that facilitate context management with remotely emulated applications are not limited to use with the Citrix MetaFrame and ICA client architecture, as other emulation architectures can be employed. When a different emulation architecture is employed, the clients may be provided with alternate application programming interfaces that allow for the collection of different types of information. Thus, the above-described implementation is merely illustrative, and simply makes use of the Citrix-provided API to collect information from which a client can be uniquely identified. The present invention is not limited to using the types of information described above, as any suitable information that uniquely identifies the client can be employed.

In an alternate embodiment of the present invention, the identifiers provided by the remote application servers to identify their associated clients need not be identical, as the client can provide information to the context manager to enable the context manager to determine that two remote applications may in fact be emulated on the same emulation client, even if they provide different identifiers. For example, if an emulation client were to use a different user ID and/or password to log into two different remote application servers, the emulation client can provide both sets of identifiers to the context manager in a manner that makes clear to the context manager that both sets of identifiers identify the same emulation client. The context manager can then use this information to determine that two remote application servers that provide different types of identifiers for an emulation client nevertheless are emulated on the same emulation client.

As should be appreciated from the foregoing, the present invention is not limited in any manner to the nature of the identifiers provided from one or more remote server applications and emulation clients to the context manager to enable the context manager to determine that the remote server applications are emulated on the same client, as numerous implementations are possible.

Figure 3:
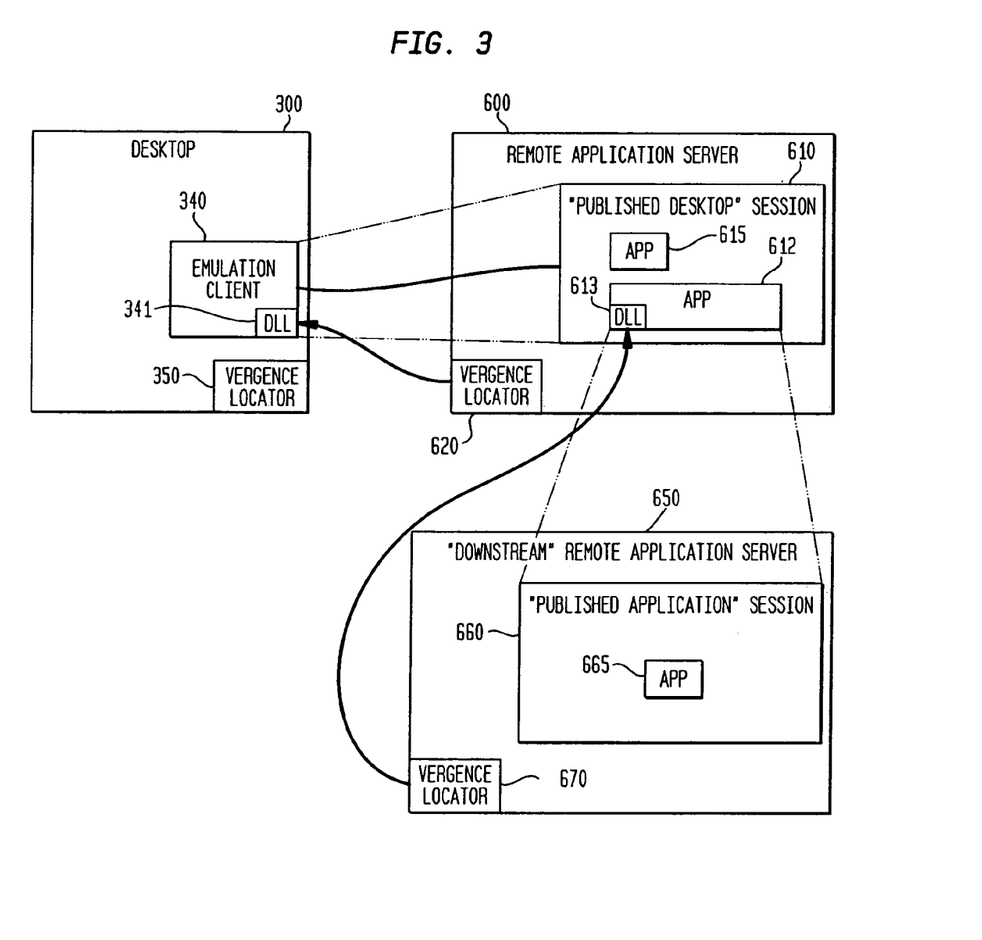
FIG. 3 depicts an exemplary system configuration having nested layers of remotely emulated applications, and on which aspects of the present invention may be implemented.

Some remote application and emulation client configurations (e.g., the Citrix MetaFrame and ICA client architecture) enable an emulation client to not only emulate specific applications, but also allow a client to emulate (or "publish") entire processing environments ("desktops"), which may include icons allowing the client to execute other applications remotely. There are numerous possibilities for the manner in which this can be configured. For example, a Citrix ICA client may emulate a desktop environment executing on a first Citrix MetaFrame server, and the desktop may provide access to one or more applications which execute on a different (or "downstream") Citrix MetaFrame server. Such a configuration is illustrated in FIG. 3. In accordance with one embodiment of the present invention, a technique is provided to verify that a remote application executing on a downstream remote application server is emulated on the same client as other context participants, and can thus participate in a context with them. In one embodiment, an identifier that uniquely identifies the emulation client is provided to the downstream remote application server, which then provides the unique identifier to the context manager for matching with an identifier that the context manager retrieves directly from the client machine, in much the same manner as described above.

In the configuration depicted in FIG. 3, emulation client 340 emulates a remote desktop session 610 executing on remote application server 600. Session 610 is provided in the form of a desktop, from which emulation client 340 may launch one or more applications (e.g., applications 612 and 615). In the configuration shown, when application 615 is launched, it is executed on the remote application server 600, within session 610. However, application 612 is a client application for a remotely executing application 665, so that when application 612 is launched, it initiates the application 655 in a session 660 on downstream remote application server 650. This may occur in a manner which is transparent to emulation client 340. During the execution of application 665, client application 612 persists within session 610 as an emulation of application 665, which facilitates communication between emulation client 340 and application 665.

In one embodiment, remote application server 600 and downstream remote application server 650 include vergence locators 620 and 670, respectively. During the process of determining whether remotely executing applications can participate in a context, the vergence locators 620 and 670 each contact their corresponding client (e.g. using the Citrix-enabled virtual channel—see 631 in FIG. 2—when in a system that employs the Citrix MetaFrame and ICA client architecture), to request that their corresponding client return a unique identifier in the manner described above. In the configuration shown in FIG. 3, the desktop is provided with a DLL 341 that provides the ability for the emulation client 340 to obtain a MAC address for a network adaptor on the desktop 300. Thus, in one embodiment, the vergence locator 620 contacts the emulation client 240 and request the MAC address. Similarly, the vergence locator 670 contacts the client on which the application 665 is emulated, which client is the application 612 executing on the remote application server 600. In accordance with one embodiment of the present invention, when the DLL 613 associated with the client application 612 receives this request, the DLL will query the server on which it is executing (i.e., server 600) to determine whether the server is a remote application server. If so, the DLL 613 will not return a MAC address for the remote application server 600, but rather, will contact the vergence locator 620 to obtain the MAC address for the client (i.e., emulation client 340) on which the remote application 612 is emulated. In this manner, both the application 615 executing on the remote application server 600 and the application 665 executing on the downstream remote application server 650 will return to the context manager the same MAC address for the desktop 300, enabling the context manager to verify that these applications are emulated on the same client and can participate together in a context.

It should be appreciated that the aspect of the present invention that relates to determining an identifier for an end of the line client on which a published application is ultimately emulated is not limited to a 2-level emulation environment as shown in FIG. 3, as the above-described techniques can be employed on deeper hierarchical configurations having any number of levels.

In the embodiment described above in connection with FIG. 3, the end of the line client machine (i.e., desktop 300) on which the remote applications are emulated has an associated DLL 341 that provides the capability to retrieve the MAC address for the client machine. As the MAC address provides a verifiable unique identifier for the client, embodiments of the present invention that are used in connection with such configurations can support context sharing amongst remote applications across numerous configurations, including different published desktops.

It should be appreciated that the aspects of the present invention described herein are not limited to use with an emulation client that has a DLL or other facility to allow for the retrieval of a unique hardware identifier. In accordance with one embodiment of the present invention for use in connection with a client that has no such ability, a restriction is placed on context sharing between remote applications, such that remote applications can only share a context if they are executing on, or remotely emulated on, the same desktop, such as the published desktop session 610 in FIG. 3. In accordance with this embodiment of the present invention, when the vergence locator 670 on the downstream remote application server 650 seeks a unique identifier for its corresponding client, the DLL 613 returns a MAC address for the remote application server 600, and also a unique identifier for the published desktop session 610. Thus, when the context manager reviews the returned identifiers to determine whether the applications 665 and 615 can share a context, it verifies that these applications are not only executing and/or emulated on the same machine (i.e., remote application server 600), but that they are in the same published desktop session 610.

As mentioned above, the computer system configuration shown in FIG. 2 is merely illustrative, as numerous other configurations are possible. For example, in the illustrative configuration of FIG. 2, the applications executing on the remote application server 600 are COM-based applications. However, it should be appreciated that web-based applications can also be implemented on a remote application server. For example, a browser can be executed on the remote application server and emulated on an emulation client such as client 340 in FIG. 2. In such a configuration, the listener 335 illustrated in FIG. 2 can be implemented on the remote application server along with the browser, and can be accessed in substantially the same manner as discussed above (e.g., through a back-channel established between the context server 400 and the vergence locator 620 on the remote application server 600).

Referring to the exemplary configuration of FIG. 2, components thereof that support context management include the context server 400, the vergence locator 350, listener 335, COM adapter 320, CM registry 352, and the CM and CP interfaces 315, 325 and 375 on the desktop, as well as the CP interface 510 for the web server, and the vergence locator 620, COM adapter 617 and CP interface 640 on the remote application server 600.

It should be appreciated from some configurations are possible wherein the desktop 300 consists solely of an emulation client for one or more remote server applications. As should be appreciated from the description above, the desktop itself need not include any components to support context management, as all of that support can be provided on the context manager 400 and one or more remote application servers 600.

It should be appreciated that although the foregoing discussion specifically describes implementing context management in a networked environment using the CCOW standard, aspects of the present invention described herein are not limited in this respect, and can be employed to implement context management in other ways that are not limited to the CCOW standard.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the present invention comprises at least one computer-readable medium (e.g., a computer memory, a floppy disk, a compact disk, a tape, etc.) encoded with a computer program (i.e., a plurality of instructions), which, when executed on a processor, performs the above-discussed functions of the embodiments of the present invention. The computer-readable medium can be transportable such that the program stored thereon can be loaded onto any computer system resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

It should be appreciated that in accordance with several embodiments of the present invention wherein processes are implemented in a computer readable medium, the computer implemented processes may, during the course of their execution, receive input manually (e.g., from a user), in the manners described above.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. In a system comprising a client, a context management (CM) server, and a network that couples the client to the CM server and includes at least one security facility which prevents the CM server from initiating a connection with the client, the client executing at least one client application that shares a context with another application for a period of time, the CM server executing a context management service to manage the context, the context comprising at least one subject data item usable by the at least one client application and the another application, the at least one subject data item having a set of values comprising a first value corresponding to the at least one client application and a second value corresponding to the another application, a method of facilitating communication between the client and the CM server, the method comprising acts of:

(a) establishing a connection, through the network, between the client and the CM server to enable communication between the CM server and the client;
(b) employing the connection to transmit one or more communications between the CM server and the client to facilitate sharing of the context by the at least one client application and the another application; and
(c) maintaining the connection between the client and the CM server for the period of time during which the at least one client application and the another application share the context.

2. The method of claim 1, wherein the act (a) further comprises establishing a backchannel connection between the client and the CM server through TCP/IP.

3. The method of claim 1, wherein the client comprises a locator utility, and wherein the act (a) comprises an act of establishing the connection between the locator utility and the CM server.

4. The method of claim 3, further comprising an act of using the connection to transmit communication from the CM server to the client for communication transactions initiated by the CM server.

5. The method of claim 4, further comprising an act of using the connection to conduct a plurality of transactions between the client and the CM server.

6. The method of claim 3, further comprising an act (c) of transmitting a communication from the CM server to the at least one client application, the act of transmitting comprising:
(c1) transmitting the communication from the CM server to the locator utility; and
(c2) relaying the communication from the locator utility to the at least one client application.

7. The method of claim 6, wherein the act (c1) comprises an act of including in the communication information that identifies the at least one of the client applications.

8. The method of claim 1, wherein the at least one client application is selected from a group consisting of a COM-based application, a browser, a client for a remotely emulated application, and an application that is emulated on a remote client.

9. The method of claim 1, wherein the context shared by the at least one client application comprises a user identity for purposes of a single sign-on for the at least one client application and the other application.

10. The method of claim 1, wherein the act (a) further comprises the client initiating the connection with the CM server.

11. The method of claim 1, wherein the system comprises a plurality of clients coupled to the server via the network, each of the plurality of clients executing at least one client application that shares the context for the period of time,
wherein the method facilitates communication between the plurality of clients and the CM server;
wherein the act (a) comprises establishing connections, through the network, between each of the plurality of clients and the CM server to enable communication between the CM server and the plurality of clients; and
wherein the act (b) comprises maintaining the connections between the plurality of clients and the CM server for the period of time during which the plurality of applications share the context.

12. The method of claim 1, wherein the first value is equal to the second value.

13. At least one computer-readable medium encoded with instructions for performing a method in a system comprising a client, a context management (CM) server, and a network that couples the client to the CM server and includes at least one security facility which prevents the CM server from initiating a connection with the client, the client executing at least one client application that shares a context with another application for a period of time, the CM server executing a context management service to manage the context, the context comprising at least one subject data item usable by the at least one client application and the another application, the at least one subject data item having a set of values comprising a first value corresponding to the at least one client application and a second value corresponding to the another application, the method for facilitating communication between the client and the CM server, the method comprising acts of:
(a) establishing a connection, through the network, between the client and the CM server to enable communication between the CM server and the client;
(b) employing the connection to transmit one or more communications between the CM server and the client to facilitate sharing of the context by the at least one client application and the another application; and
(c) maintaining the connection between the client and the CM server for the period of time during which the at least one client application and the another application share the context.

14. The at least one computer-readable medium of claim 13, wherein the act (a) further comprises establishing a backchannel connection between the client and the CM server through TCP/IP.

15. The at least one computer-readable medium of claim 14, wherein the network includes security facilities that prevent the CM server from establishing a connection to the client.

16. The at least one computer-readable medium of claim 13, wherein the client comprises a locator utility, and wherein the act (a) comprises an act of establishing the connection between the locator utility and the CM server.

17. The at least one computer-readable medium of claim 16, wherein the method further comprises an act of using the connection to transmit communication from the CM server to the client for communication transactions initiated by the CM server.

18. The at least one computer-readable medium of claim 17, wherein the method further comprises using the connection to conduct a plurality of transactions between the client and the CM server.

19. The at least one computer-readable medium of claim 16, wherein the method further comprises an act (c) of transmitting a communication from the CM server to the at least one client application, the act of transmitting comprising:
(c1) transmitting the communication from the CM server to the locator utility; and
(c2) relaying the communication from the locator utility to the at least one client application.

20. The at least one computer-readable medium of claim 19, wherein the act (c1) comprises an act of including in the communication information that identifies the at least one of the client applications.

21. The at least one computer-readable medium of claim 13, wherein the at least one client application is selected from a group consisting of a COM-based application, a browser, a client for a remotely emulated application, and an application that is emulated on a remote client.

22. The at least one computer-readable medium of claim 13, wherein the context shared by the at least one client application comprises a user identity for purposes of a single sign-on for the at least one client application and the other application.

23. The at least one computer-readable medium of claim 13, wherein the act (a) further comprises the client initiating the connection with the CM server.

24. The at least one computer-readable medium of claim 13, wherein the system comprises a plurality of clients coupled to the server via the network, each of the plurality of clients executing at least one client application that shares the context for the period of time, wherein the method facilitates communication between the plurality of clients and the CM server, wherein the act (a) comprises establishing connections, through the network, between each of the plurality of clients and the CM server to enable communication between the CM server and the plurality of clients; and wherein the act (b) comprises maintaining the connections between the plurality of clients and the CM server for the period of time during which the plurality of applications share the context.

25. The at least one computer-readable medium of claim 13, wherein the first value is equal to the second value.

26. A context management server for use in a system comprising a client, the context management servers, and a network that couples the client to the context management server and includes at least one security facility which prevents the context management server from initiating a connection with the client, the client executing at least one client application that shares a context with another application for a period of time, the context comprising at least one subject data item usable by the at least one client application and the another application, the at least one subject data item having a set of values comprising a first value corresponding to the at least one client application and a second value corresponding to the another application, the context management server comprising:
  at least one processor to execute a context management service to manage the context; and
  at least one controller that employs a connection through the network to transmit one or more communications to the client to facilitate sharing of the context by the at least one client application and the another application, and maintains the connection with the client for the period of time during which the at least one client application and the another application share the context.

27. The context management server of claim 26, wherein the context management server further maintains a backchannel connection between the client and the context management server through TCP/IP.

28. The context management server of claim 27, in combination with the network and the client to form the system, wherein the context management server is prevented by security facilities on the network that prevent the context management server from establishing a connection to the client.

29. The context management server of claim 26, wherein the client comprises a locator utility, and wherein the controller maintains the connection between the locator utility and the context management server.

30. The context management server of claim 29, wherein the controller uses the connection to transmit communication from the context management server to the client for communication transactions initiated by the context management server.

31. The context management server of claim 30, wherein the controller uses the connection to conduct a plurality of transactions between the client and the context management server.

32. The context management server of claim 29, wherein the controller transmits a communication via the locator utility to the at least one client application.

33. The context management server of claim 32, wherein the controller further includes in the communication information that identifies the at least one of the client applications.

34. The context management server of claim 26, wherein the context shared by the at least one client application comprises a user identity for purposes of a single sign-on for the at least one client application and the other application.

35. The context management server of claim 26, wherein the controller maintains a network connection which is initiated by the client with the context management server.

36. The context management server of claim 26, wherein the system comprises a plurality of clients coupled to the server via the network, each of the plurality of clients executing at least one client application that shares the context for the period of time, and wherein the controller is further adapted to:
  establish connections, through the network, between each of the plurality of clients and the CM server to enable communication between the CM server and the plurality of clients; and
  maintain the connections between the plurality of clients and the CM server for the period of time during which the plurality of applications share the context.

37. The context management server of claim 26, wherein the first value is equal to the second value.

38. A client computer for use in a system comprising the client computer, a context management (CM) servers, and a network that couples the client computer to the CM server and includes at least one security facility which prevents the CM server from initiating a connection with the client, the client computer comprising:
  at least one processor to execute at least one client application that shares a context with another application for a period of time, the context comprising at least one subject data item usable by the at least one client application and the another application, the at least one subject data item having a set of values comprising a first value corresponding to the at least one client application and a second value corresponding to the another application; and
  at least one controller that employs a network connection to transmit one or more communications to the CM server to facilitate sharing of the context by the at least one client application and the another application, and maintains the connection with the CM server for the period of time during which the at least one client application and the another application share the context.

39. The client computer of claim 38, wherein the connection is a backchannel connection established between the client computer and the CM server through TCP/IP.

40. The client computer of claim 39, wherein the network includes security facilities that prevent the CM server from establishing a connection to the client computer.

41. The client computer of claim 38, wherein the client computer further comprises a locator utility, and wherein the connection is established between the locator utility and the CM server.

42. The client computer of claim 41, wherein the client computer is adapted to receive over the connection communications transmitted from the CM server to the client for communication transactions initiated by the CM server.

43. The client computer of claim 42, wherein the at least one controller uses the connection to conduct a plurality of transactions between the client computer and the CM server.

44. The client computer of claim 41, wherein the locator utility is adapted to receive communications from the CM server to the at least one client application, and to relay the communications from the locator utility to the at least one client application.

45. The client computer of claim 44, wherein the communications include information that identifies the at least one of the client applications.

46. The client computer of claim 38, wherein the at least one client application is selected from a group consisting of a COM-based application, a browser, a client for a remotely emulated application, and an application that is emulated on a remote client.

47. The client computer of claim 38, wherein the context shared by the at least one client application comprises a user identity for purposes of a single sign-on for the at least one client application and the other application.

48. The client computer of claim 38, wherein the at least one controller is adapted to initiate the connection with the CM server.

49. The client computer of claim 38, wherein the first value is equal to the second value.

* * * * *